(12) United States Patent
Suzuki (10) Patent No.: US 8,721,609 B2
(45) Date of Patent: May 13, 2014

(54) ABSORPTIVE ARTICLE

(75) Inventor: Youko Suzuki, Sakura (JP)

(73) Assignee: Daiopaper Corporation, Shikokuchuo-Shi (JP)

( * ) Notice: Subject to any disclaimer, the term of this patent is extended or adjusted under 35 U.S.C. 154(b) by 63 days.

(21) Appl. No.: 13/499,228

(22) PCT Filed: Sep. 16, 2010

(86) PCT No.: PCT/JP2010/066064
§ 371 (c)(1),
(2), (4) Date: Mar. 29, 2012

(87) PCT Pub. No.: WO2011/040257
PCT Pub. Date: Apr. 7, 2011

(65) Prior Publication Data
US 2012/0184935 A1    Jul. 19, 2012

(30) Foreign Application Priority Data
Sep. 30, 2009    (JP) .................................. 2009-227439

(51) Int. Cl.
*A61F 13/15*    (2006.01)
*A61F 13/49*    (2006.01)
(52) U.S. Cl.
USPC ................................ 604/385.11; 604/385.01
(58) Field of Classification Search
USPC ................................ 604/385.01, 385.11, 394
See application file for complete search history.

(56) References Cited

U.S. PATENT DOCUMENTS

| | | | |
|---|---|---|---|
| 6,394,991 B1 | 5/2002 | Takei et al. | |
| 6,764,475 B1 | 7/2004 | Olson | |
| 2003/0009142 A1* | 1/2003 | Nukina et al. | 604/380 |
| 2005/0113791 A1* | 5/2005 | Neubauer et al. | 604/387 |
| 2006/0271009 A1* | 11/2006 | Cartier et al. | 604/385.31 |
| 2009/0088713 A1* | 4/2009 | Norrby | 604/365 |

FOREIGN PATENT DOCUMENTS

| | | | |
|---|---|---|---|
| JP | 7-255773 A | | 10/1995 |
| JP | 10137288 A | * | 5/1998 |
| JP | 2001-120595 A | | 5/2001 |

(Continued)

OTHER PUBLICATIONS

International Search Report dated Dec. 14, 2010 issued in International Appln. No. PCT/JP2010/066064.

(Continued)

*Primary Examiner* — Jackie Ho
*Assistant Examiner* — Kathryn E Ditmer
(74) *Attorney, Agent, or Firm* — Holtz, Holtz, Goodman & Chick (57) ABSTRACT

An absorptive article (1) has: an absorptive body (10) which includes an absorption body; and an exterior body (20) which is provided to the outer surface side of the absorptive body (10) and which is provided with a belly-side portion (F) and a back-side portion (B). The belly-side portion (F) and the back-side portion (B) are joined together at joint sections (21, 22). Reduced strength regions (T) and unreduced strength regions (S) are disposed between the belly-side section (F) and the back-side section (B) at the positions of the joint sections (21, 22). A reduced strength region (T) includes a joint strength-reducing material for reducing the joint strength between the joint sections (21, 22), and an unreduced strength region (S) includes no joint strength-reducing material.

17 Claims, 11 Drawing Sheets

(56) References Cited

FOREIGN PATENT DOCUMENTS

| | | | |
|---|---|---|---|
| JP | 2002-291801 A | 10/2002 |
| JP | 2004-267335 A | 9/2004 |
| JP | 2006-6780 A | 1/2006 |
| JP | 2008-136794 A | 6/2008 |
| JP | 2008-212485 A | 9/2008 |
| JP | 2009-034209 A | 2/2009 |
| JP | 2009-131539 A | 6/2009 |
| JP | 2009-148465 A | 7/2009 |

OTHER PUBLICATIONS

Chinese Office Action dated May 31, 2013 (and English translation thereof) in counterpart Chinese Application No. 201080043958.9.

Extended European Search Report (EESR) dated Nov. 19, 2013 (in English) in counterpart European Extended Application No. 10820376.1.

Chinese Office Action dated Feb. 20, 2014 (and English translation there of) issued in counterpart Chinese Application No. 201080043958.9.

* cited by examiner

ABSORPTIVE ARTICLE

This application is a U.S. National Phase Application under 35 USC 371 of International Application PCT/JP2010/006,6064 filed Sep. 16, 2010.

TECHNICAL FIELD

The present invention relates to an absorptive article.

BACKGROUND ART

Conventionally, a disposable paper diaper is known as an absorptive article. As a disposable paper diaper, a pants-type and a tape-type paper diaper is known.

Among these, generally, the pants-type disposable paper diaper includes an absorptive body which includes an absorption body and an exterior sheet provided as one with the absorptive body on the outer surface side. In a product state, a belly-side portion and a back-side portion of the exterior sheet are joined at joint sections of both side ends of the belly-side portion and the back-side portion to form a waist opening section and a pair of left and right leg opening sections.

With such pants-type disposable diaper, it is preferable that the joint section is not peeled improperly when the disposable diaper is worn and that it is easy to peel and separate when the disposable diaper is disposed.

Therefore, for example, a technique is proposed where joint strength is weakened by applying an adhesive between each sheet laminated at both side end portions of the exterior sheet and the joint strength is evened by applying a different amount of adhesive according to the number of sheets laminated at both side end portions (for example, see patent document 1).

PRIOR ART DOCUMENT

Patent Document

Patent Document 1: Japanese Patent Application Laid-Open Publication No. 2009-148465

DISCLOSURE OF THE INVENTION

Problems to be Solved by the Invention

However, with the conventional method, the joint strength is generally reduced which merely enhances the easiness of peeling, and it is difficult to say that both the strength of the joint section and the easiness of peeling are enhanced.

The object of the present invention is to provide an absorptive article in which both the strength of the joint section and the easiness of peeling are enhanced.

Means for Solving the Problem

In order to achieve the above object, an absorptive article according to a first aspect of the present invention comprises:
an absorptive body which includes an absorption body; and
an exterior body which is provided to an outer surface side of the absorptive body and which is provided with a belly-side portion which is located on a belly side of a human body when the absorptive article is worn and a back-side portion which is located on a back side of a human body when the absorptive article is worn;
wherein a hip opening section and a pair of left and right leg opening sections are formed in the absorptive article by joining, using heat sealing or ultrasonic sealing, the belly-side portion and the back-side portion of the exterior body at joint sections at both side ends of the belly-side portion and the back-side portion; and
wherein the absorptive article includes a reduced strength region, which is disposed with a joint strength reducing material for reducing the joint strength between the joint sections, and an unreduced strength region, which is not disposed with the joint strength reducing material, between the belly-side portion and the back-side portion of the joint sections.

According to a second aspect of the present invention, in the absorptive article of the first aspect of the present invention, the reduced strength region and the unreduced strength region are provided alternately continuously along a longitudinal direction of the joint section.

According to a third aspect of the present invention, in the absorptive article of the first aspect of the present invention:
the reduced strength region includes a first reduced strength section and a second reduced strength section arranged parallel along a width direction of the joint section; and
the first reduced strength section is provided continuously from an upper end portion to a lower end portion of the joint section.

According to a fourth aspect of the present invention, in the absorptive article of the first aspect of the present invention, the unreduced strength region is provided at an upper end portion and/or a lower end portion of the joint section.

According to a fifth aspect of the present invention, in the absorptive article of the first aspect of the present invention, the joint strength reducing material is an adhesive, paper, nonwoven fabric or a base material on which oil agent is applied.

According to a sixth aspect of the present invention, in the absorptive article of the first aspect of the present invention, a predetermined color is added to the joint strength reducing material.

Advantageous Effect of the Invention

According to the present invention, a hip opening section and a pair of left and right leg opening sections are formed in the absorptive article by joining, using heat sealing or ultrasonic sealing, the belly-side portion and the back-side portion of the exterior body together at joint sections located at both side ends of the belly-side portion and the back-side portion. Reduced strength regions, which are disposed with a joint strength-reducing material for reducing the joint strength between the joint sections, and unreduced strength regions, which are not disposed with joint strength-reducing material, are disposed between the belly-side section and the back-side section at the joint sections.

Therefore, when the absorptive article is worn, it is possible to prevent improper peeling of the joint section by the region with strong joint strength while it is possible to easily peel from the region with reduced joint strength as the cutting section when deliberately peeling. Therefore, it is possible to achieve both enhanced strength and increased easiness of peeling of the joint sections.

EMBODIMENT FOR CARRYING OUT THE INVENTION

Below, an embodiment of the present invention is described in detail using the diagrams. However, the scope of the invention is not limited to the illustrated examples.

The present embodiment describes an example of a pants-type disposable paper diaper (hereinafter referred to as "paper diaper") as an absorptive article.

As shown in FIG. 1 to FIG. 5, the paper diaper 1 includes an absorptive body 10 which includes an absorption body 13 and an exterior body 20 which is provided to the outer surface side of the absorptive body 10 and is provided with a belly-side portion F which is located on a belly side of a human body when the paper diaper 1 is worn and with a back-side portion B which is located on the back side of the human body when the paper diaper 1 is worn.

In the paper diaper 1, a hip opening section W and a pair of left and right leg opening sections L are formed by joining the belly-side portion F and the back-side portion B of the exterior body 20 together at joint sections (21, 22) located at both side ends of the belly-side portion F and the back-side portion B and a crotch portion M is formed between the pair of left and right leg opening sections L.

Figure 1:
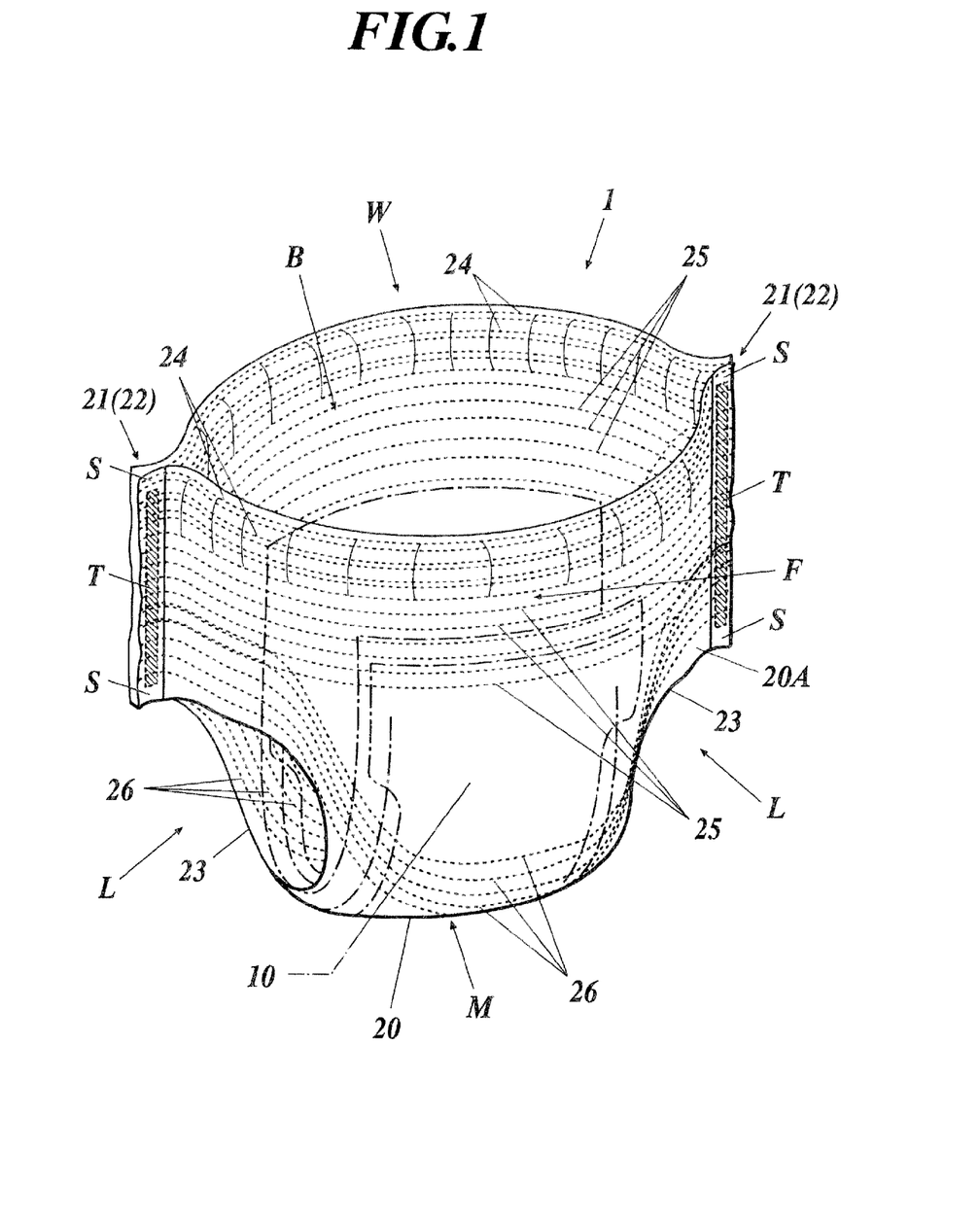
FIG. 1 is a diagram showing an external appearance of a product state of a paper diaper of a first embodiment.
Figure 2:
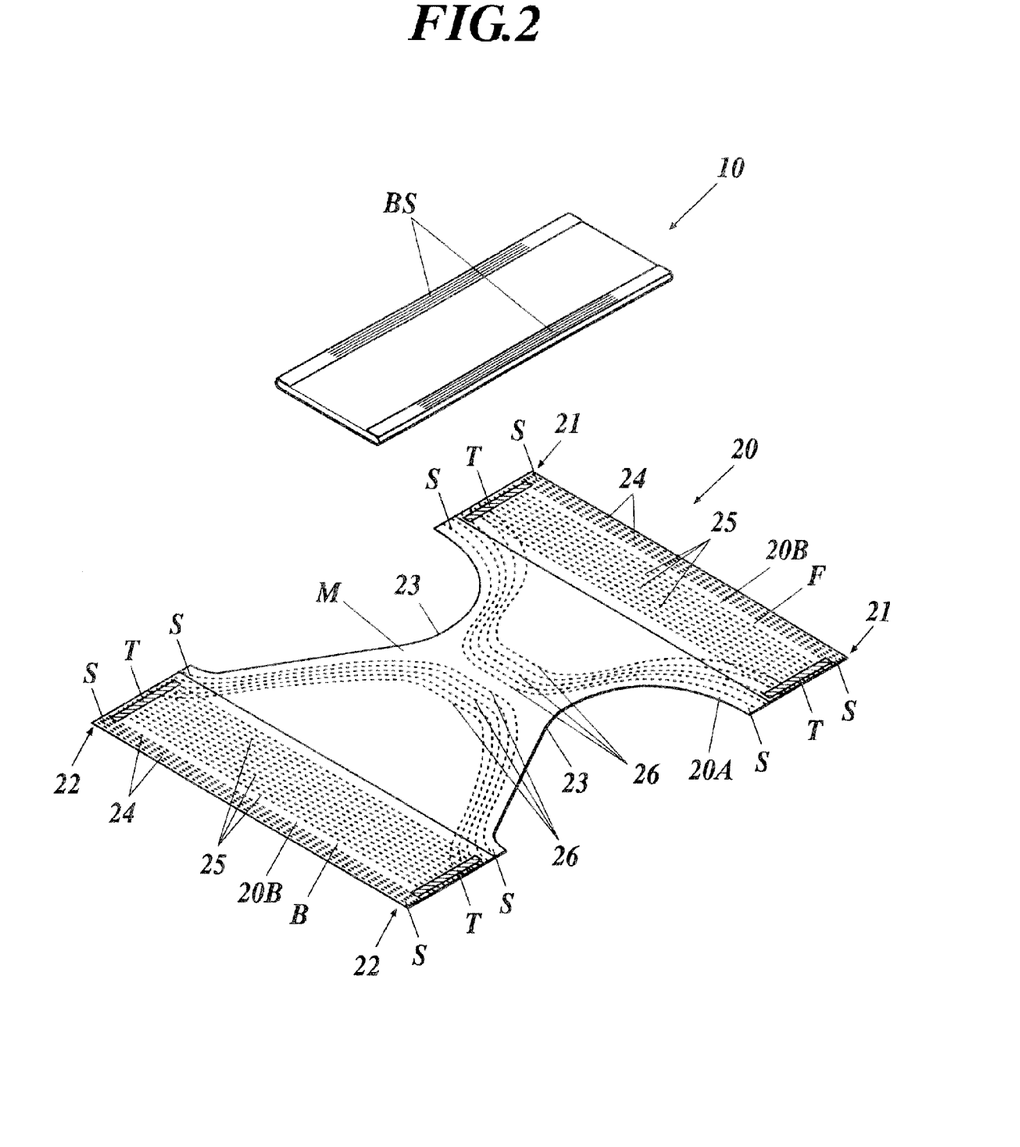
FIG. 2 is an exploded perspective diagram showing a paper diaper shown in FIG. 1.
Figure 3:
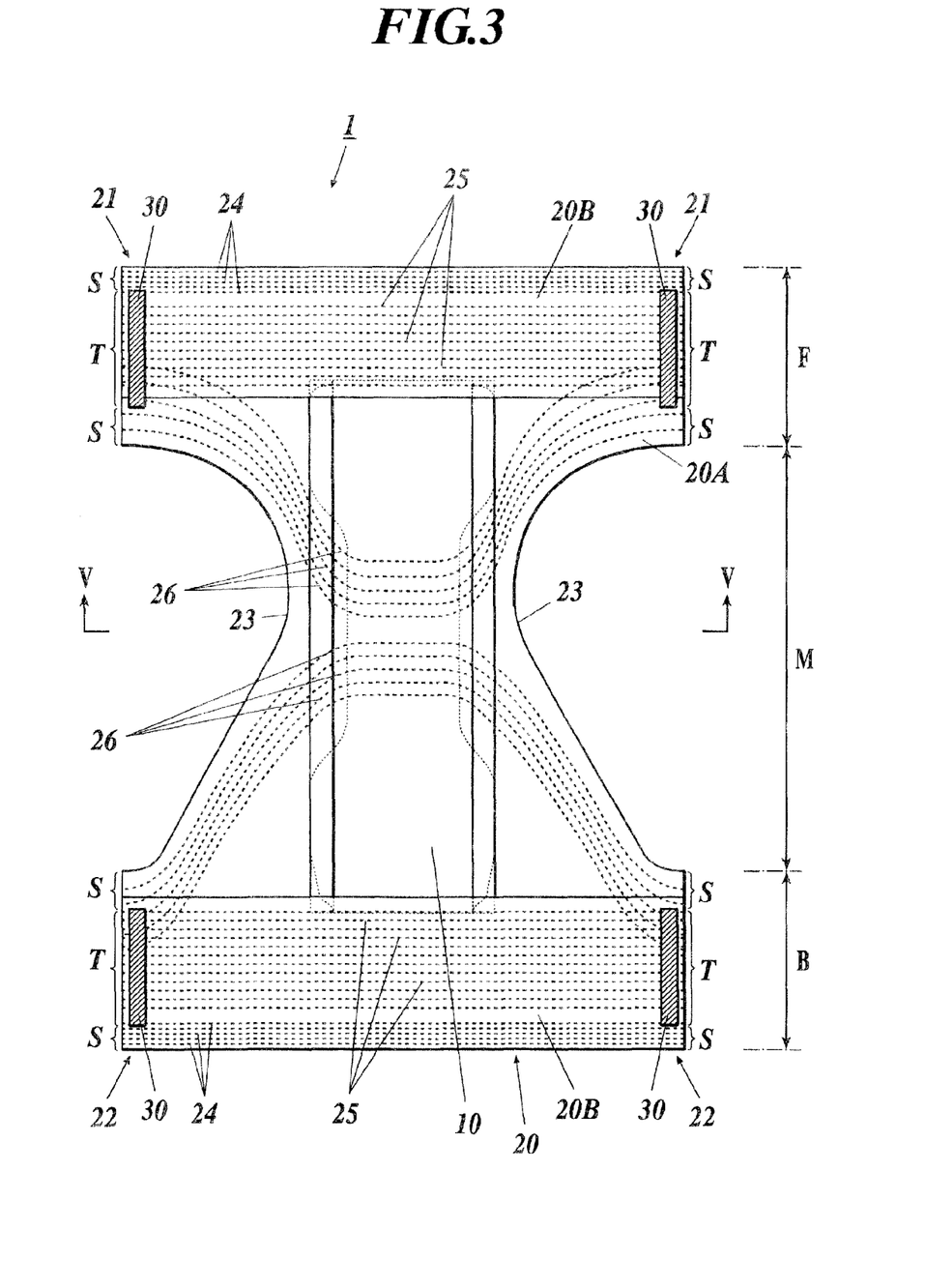
FIG. 3 is a developed diagram showing an exterior body of the paper diaper shown in FIG. 1.

As shown in FIG. 2, in the paper diaper 1, the outer surface side of the absorptive body 10 is adhered to the inner surface of the external body 20, which is to be the body side when the paper diaper is worn, by an adhesive such as hot melt, etc., and the absorptive body 10 and the external body 20 are formed as one. Then, the crotch portion M of the external body 20 is folded with the absorptive article 10 to fold the belly-side portion F of the external body 20 on the back-side portion B of the external body 20, and the joint section 21 and the joint section 22 are joined respectively at the left and right portions by heat sealing or ultrasonic sealing. With this, the paper diaper 1 shown in FIG. 1 is formed.

(Absorptive Body)

Figure 4:
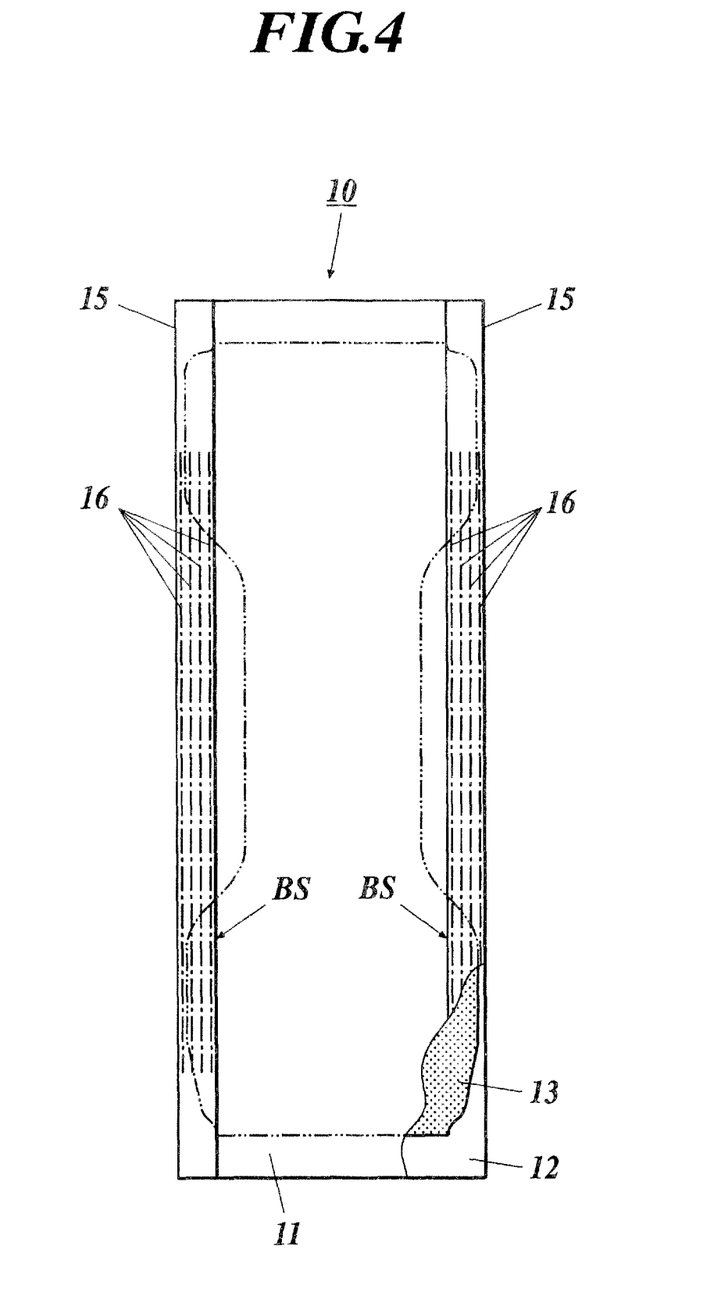
FIG. 4 is a planar diagram showing an absorptive body of the paper diaper shown in FIG. 1.
Figure 5:
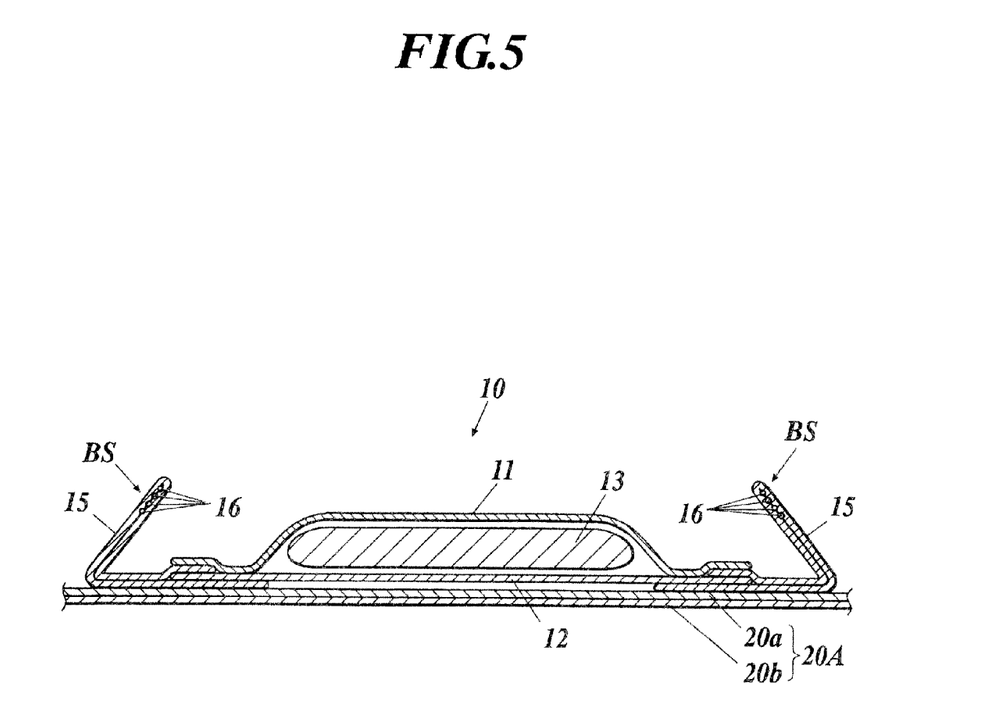
FIG. 5 is a cross-sectional diagram along line V-V shown in FIG. 3.

As shown in FIG. 4 and FIG. 5, the absorptive body 10 is a structure including a liquid permeable surface sheet 11 including a nonwoven fabric and a waterproof sheet 12 including polyethylene, etc., with an absorption body 13 between the liquid permeable surface sheet 11 and the waterproof sheet 12, and the absorption body 13 is formed by combining an absorptive material such as cotton, pulp, etc., a sheet shaped base such as fiber, film, etc. and a high water absorptive resin. The absorptive body 10 absorbs and holds aqueous component such as urine, etc. which is a biological fluid.

The absorptive body 10 is provided from the belly-side portion F to the back-side portion B of the exterior body 20 on the crotch portion M formed extending toward the outer side in the width direction than the absorptive body 10. A pair of left and right standing gathers BS is provided extending in the longitudinal direction on both end portions in the width direction of the absorptive body 10.

For example, the absorption body 13 is shaped to have a substantial sandglass shape from a planar view. The width dimension of the absorption body 13 is a size which does not have a rough feel when the absorption body 13 touches the body of the wearer.

The absorption body 13 can be surrounded by crepe paper (not shown) in order to maintain the shape and to enhance diffusibility of the biological fluid which permeates the liquid permeable surface sheet 11.

As material of the nonwoven fabric which forms the liquid permeable surface sheet 11 covering the front surface side (surface side in contact with skin) of the absorption body 13, either natural fiber or synthetic fiber can be used. As examples of natural fiber, there are cotton, cellulose (wood pulp), sheep wool, silk and the like. As synthetic fiber, polypropylene (PP), polyethylene (PE), nylon, polyester (PET), acryl and the like, or PE/PP mixed nonwoven fabric, PE/PET mixed nonwoven fabric or bicomponent fiber (mixed fiber) suitably combining the above material can be used.

As a method of producing a nonwoven fabric from a fibrous material, a well known method can be suitably used and any method such as chemical bonding, thermal bonding, spunlace, etc. can be used. For synthetic fiber, etc., any method such as spunbond method, meltblown method, etc. or a combination of the above bonding method, etc. can be used to produce the nonwoven fabric.

Among the above processing methods, nonwoven fabric by spunlace method excels in the point of having high flexibility and draping properties, and nonwoven fabric by thermal bonding method excels in the point of being large for its weight and being soft.

Moreover, when a large number of through holes are formed in the liquid permeable surface sheet 11, urine, etc. can be absorbed swiftly and excels in having a dry touch.

The waterproof sheet 12 covering the rear surface side (surface side not in contact with skin) of the absorption body 13 includes water shielding properties to prevent aqueous components which pass through the absorption body 13 from leaking to the exterior body 20 side and non permeable plastic sheet such as polyethylene or polypropylene is used. A sheet including moisture permeability is preferably used from the view point of preventing stuffiness. The water shielding and moisture permeable sheet is a microporous sheet obtained by forming a sheet by melting and kneading an inorganic filler in an olefin resin such as polyethylene, polypropylene, etc. and then extending the sheet in a uniaxial or biaxial direction. When the sheet is a microporous sheet, stiffness is reduced than a nonporous sheet if the sheet thickness is the same, and therefore the microporous sheet excels in the point of flexibility.

It is preferable to use an opaque sheet as the waterproof sheet 12 so that it is difficult to see brown color of defecation, urine, etc. As an opaque waterproof sheet 12, a film formed by adding pigment or filler such as calcium carbonate, titanium oxide, zinc oxide, white carbon, clay, talc, barium sulfate, etc. in olefin resin or plastic is preferably used.

The standing gather BS is formed by folding non-permeable gather nonwoven fabric 15 in half and placing a side edge section of the waterproof sheet 12 in between at the base end portion and the folded together surface is fixed by, for example hot melting, heat sealing, ultrasonic sealing, etc. A side edge section of the permeable surface sheet 11 is adhered to the upper surface side of the base end portion of the gather nonwoven fabric 15 doubled by folding.

Regarding the gather nonwoven fabric 15, the middle portion in the longitudinal direction of the absorptive body 10 is the free end portion (standing end portion) which forms the standing gather BS and the front and rear end portion in the longitudinal direction is the fixed section which is folded inside the upper surface side of the absorptive body 10 and fixed by hot melt adhesive, etc.

A plurality of threadlike elastic stretching members 16, etc. are provided at a standing tip end portion of the gather nonwoven fabric 15. The threadlike elastic stretching members 16, etc. are provided so that the gather nonwoven fabric 15 stands by elastic stretching strength to form the standing gather BS.

The material fiber included in the gather nonwoven fabric 15 includes the same material as the nonwoven fabric which forms the above described liquid permeable surface sheet 11 and the producing method of the nonwoven fabric is almost the same. Specifically, it is preferable to use a nonwoven fabric with reduced measuring weight and enhanced air permeability to prevent stuffiness. As the gather nonwoven fabric 15, water repellent processed nonwoven fabric with coating by water repellant material such as silicon series, paraffin metal series, alkyl chromium chloride series can be used to prevent permeation of urine, etc. as well as to prevent rash and to enhance feel (dry feel) of the skin.

(Exterior Body)

As shown in FIG. 1 to FIG. 5, the exterior body 20 includes an outer layer sheet 20A which forms the exterior body 20. The outer layer sheet 20A is composed by adhering two nonwoven fabrics which are upper layer nonwoven fabric 20a and lower layer nonwoven fabric 20b, and later described various types of threadlike elastic members are arranged between the upper layer nonwoven fabric 20a and the lower layer nonwoven fabric 20b to provide stretching properties.

On the inner side (surface side in contact with skin) of the outer layer sheet 20A, the torso sheets 20B, 20B are provided on an upper surface of the upper layer nonwoven fabric 20a in the belly-side portion F and the back-side portion B to realize preferable fit.

In the exterior body 20, a leg cut line 23 is formed in a depressed shape to provide the leg opening sections L to each of the middle side section of the exterior body 20, and the exterior body 20 includes the crotch portion M which covers around the crotch of the wearer of the paper diaper 1, the belly-side portion F which is positioned in the front end side of the crotch portion M and covers the belly portion of the wearer, and the back-side portion B which is positioned in the rear end side of the crotch portion M and covers the back portion of the wearer. The planer shape of the exterior body 20 forms a mock sandglass shape as a whole.

A joint section 21 is formed on a width direction of both end portions of the belly-side portion F to join with the back-side portion B. A joint section 22 is formed on a width direction of both end portions of the back-side portion B to join with the belly-side portion F.

The joint sections 21, 22 include a predetermined width in the up and down direction from the opening end portion side of the hip opening section W to the leg opening section L including the leg cut line 23 in the respective belly-side portion F and the back-side portion B.

Regarding the joint sections 21, 22, the direction from the opening end portion of the hip opening section W to the leg opening section L is to be the longitudinal direction of the joint sections 21, 22, and the direction orthogonal to the longitudinal direction is to be the width direction of the joint sections 21, 22.

The joint section 21 and the joint section 22 are joined respectively at the left and right portions by heat sealing or ultrasonic sealing.

Between the joined joint sections 21, 22, reduced strength regions T which is provided with adhesive 30 such as hot melt, etc. as a joint strength reducing material for reducing the joint strength and unreduced strength region S which is not provided with adhesive 30 are formed.

In other words, by inserting adhesive 30 between the joint sections 21, 22, the joint strength of the region inserted with adhesive 30 is to be weaker than the joint strength of the region joined by heat sealing or ultrasonic sealing.

Figure 6A:
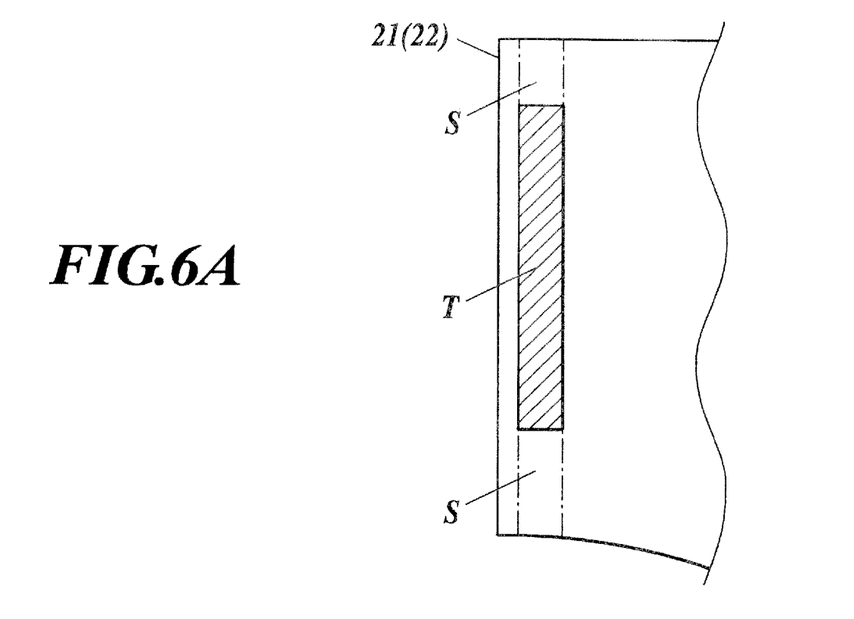
FIG. 6A is an enlarged schematic diagram showing a joint section of a paper diaper shown in FIG. 1.

Specifically, as shown in FIG. 6A, the reduced strength regions T are provided in the middle portion of the region from the hip opening section W to the leg opening section L in the joint sections 21, 22 and the unreduced strength regions S are provided at the upper end portion (end portion of the hip opening section W side) and the lower end portion (end portion of the leg opening section L side) of the joint sections 21, 22.

Therefore, the strength near the hip opening section W and the leg opening section L is strong due to the unreduced strength regions S and the strength of the middle portion is weak due to the strength reducing regions T.

The reduced strength regions T function as a cutting section to enable easy peeling and separating when the paper diaper 1 is disposed. The unreduced strength regions S maintain strength so that the paper diaper 1 is not peeled improperly when the paper diaper 1 is worn.

The shape of the reduced strength regions T and the unreduced strength regions S and the area of applying adhesive can be suitably set according to type and amount of adhesive.

Figure 6B:
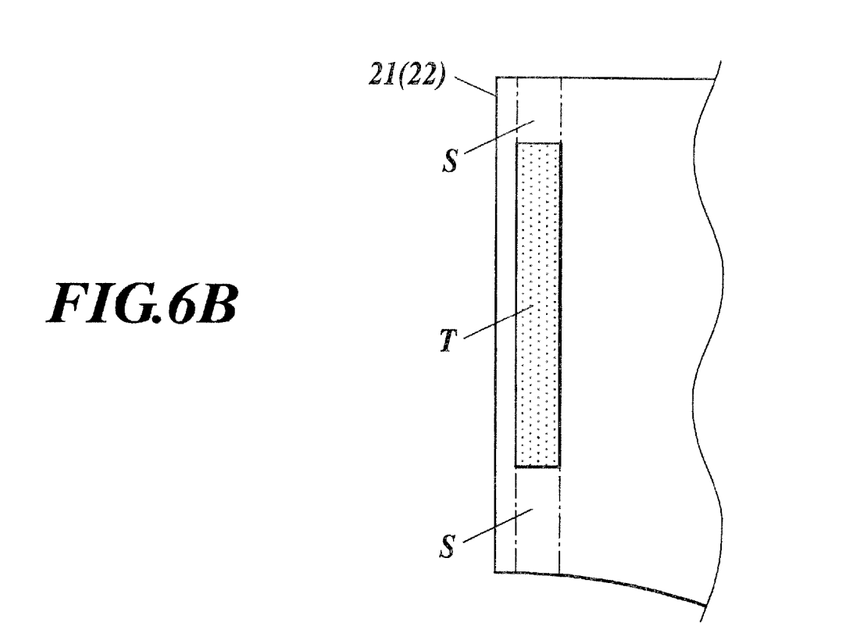
FIG. 6B is a diagram showing the joint section shown in FIG. 6A in a colored state.

As shown in FIG. 6B, it is preferable to add predetermined color to the adhesive 30 as the joint strength reducing material.

The color used is not particularly limited, and for example, one or a plurality of colors can be used among a deep color such as blue, green, orange, etc. or a light color such as pink, etc. With this, the design of the paper diaper 1 can be enhanced.

As the joint strength reducing material, for example, paper, nonwoven fabric, base material on which oil agent is applied, etc. can be used instead of adhesive.

When paper or nonwoven fabric is inserted between the joint sections 21, 22 joined by heat sealing or ultrasonic sealing, the joint strength can be reduced even more compared to adhesive.

When a base material on which oil agent is applied is inserted in between the joint sections 21, 22, the joint strength can be reduced even more compared to adhesive, and flexibility and smoothness can be achieved because the oil agent is impregnated in the inserted region.

As the joint strength reducing material, a plurality of material can be selected from adhesive, paper, nonwoven fabric and base material on which oil agent is applied and can be used together.

The exterior body 20 includes a plurality of waist elastic members 24, etc. provided in each of the belly-side portion F and the back-side portion B on the opening end portion side (upper side) of the hip opening section W, a plurality of hip elastic members 25, etc. provided in each of the belly-side portion F and the back-side portion B extending in a direction along the hip from one of the joint sections 21, 22 to the other of the joint sections 21, 22, and a plurality of leg elastic members 26, etc. provided in each of the belly-side portion F and the back-side portion B extending from the joint sections 21, 22 along the leg cut line 23 (edge section) of the leg opening section L to the crotch portion M side.

The waist elastic member 24 is a plurality of thread rubber like elastic members provided with an interval in the up and down direction near the hip opening section W in the range of the width in the up and down direction of the joint sections 21, 22 where the belly-side portion F and the back-side portion B are joined. The waist elastic member 24 is provided with stretching strength to secure around the waist portion of the body in order to wear the paper diaper 1 on the body.

The hip elastic member 25 is a plurality of thread rubber like elastic stretching members provided substantially parallel to each other in a predetermined interval in the up and down direction on the crotch portion M side than the waist elastic member 24 in each of the belly-side portion F and the back-side portion B. The hip elastic member 25 is provided with stretching strength to secure around the hip portion of the belly-side portion F and the back-side portion B. The plurality of hip elastic members 25, etc. are provided in a predetermined width and range in the exterior body 20 to closely fit the entire surface of the belly-side portion F and the back-side portion B to the body.

The leg elastic member 26 is a plurality of thread rubber like elastic stretching members provided separately from the hip elastic member 25 in the belly-side portion F and the back-side portion B. The plurality of leg elastic members 26, etc. are provided in a predetermined width and range in the exterior body 20 to closely fit the leg portion of the exterior body 20 to the body.

Specifically, the leg elastic member 26 is provided to extend from one of the joint sections 21, 22 of the belly-side portion F and the back-side portion B substantially along the leg cut line 23 to the crotch portion M side and to bypass the crotch portion M substantially along the leg cut line 23 of the other side to reach the other of the joint sections 21, 22.

As described above, the paper diaper 1 of the present embodiment includes the reduced strength regions T which is provided with adhesive 30 as a joint strength reducing material for reducing the joint strength between the joint sections 21, 22 and the unreduced strength regions S which is not provided with the joint strength reducing material between the belly-side portion F and the back-side portion B of the joint sections 21, 22.

Consequently, when the paper diaper 1 is worn, even if the paper diaper 1 for example, moves up and down, the necessary strength is maintained by the unreduced strength region S and the paper diaper 1 is not peeled improperly. When the paper diaper 1 is disposed, the reduced strength region T functions as a cutting section and peeling and separating can be easily performed.

In other words, regions with strong joint strength and regions with weak joint strength can be formed to achieve both enhanced strength and increased easiness of peeling of the joint sections 21, 22.

According to the paper diaper 1 of the present embodiment, the unreduced strength regions S are provided in the upper end portion and the lower end portion of the joint sections 21, 22. Consequently, it is difficult to peel even when force is applied to the upper end portion and the lower end portion, and the structure includes strength.

According to the paper diaper 1 of the present embodiment, as joint strength reducing material, there is adhesive, paper, nonwoven fabric or base material on which oil agent is applied. Consequently, highly versatile material can be suitably used and the joint strength of the joint sections 21, 22 can be adjusted.

According to the paper diaper 1 of the present embodiment, predetermined color is applied to the joint strength reducing material. Consequently, color is added to the reduced strength region T and design can be enhanced.

<Modification 1>

Figure 7:
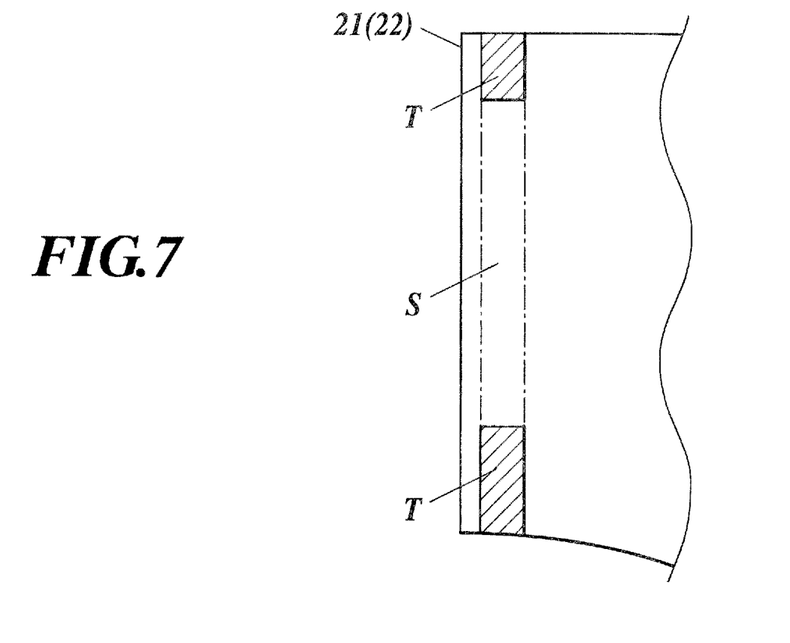
FIG. 7 is a diagram showing a joint section of a paper diaper of modification 1.

As shown in FIG. 7, in the present embodiment, the reduced strength region T can be provided in the upper end portion (end portion of the hip opening section W side) and the lower end portion (end portion of the leg opening section L side) of the joint sections 21, 22 and the unreduced strength region S can be provided in the middle portion of the region from the hip opening section W to the leg opening section L in the joint sections 21, 22.

According to the modification 1, the joint strength reducing region T is provided in the upper end portion and the lower end portion of the joint sections 21, 22. Consequently, it is possible to realize a configuration in which it is easy to peel when force is applied to the upper end portion and the lower end portion.

<Modification 2>

Figure 8A:
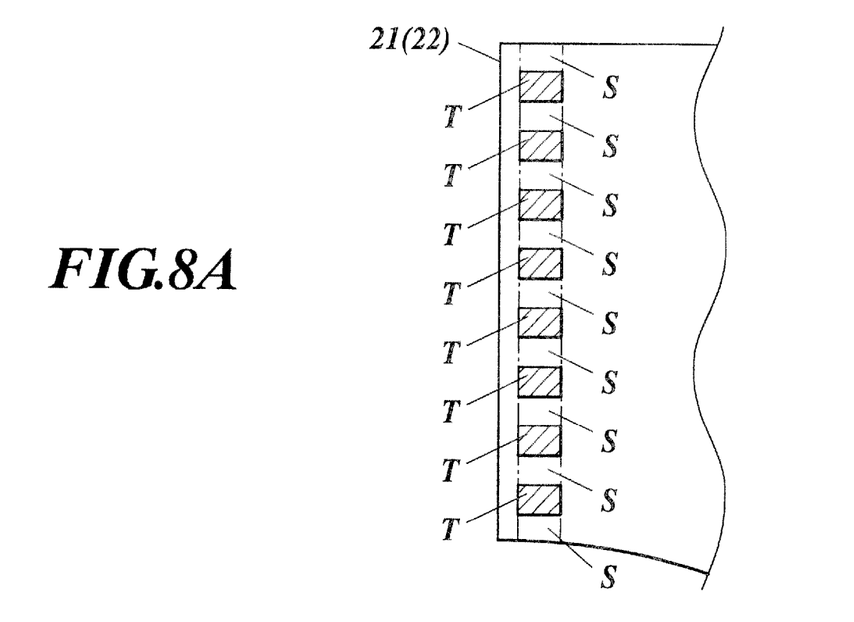
FIG. 8A is a diagram showing a joint section of a paper diaper of modification 2.
Figure 8B:
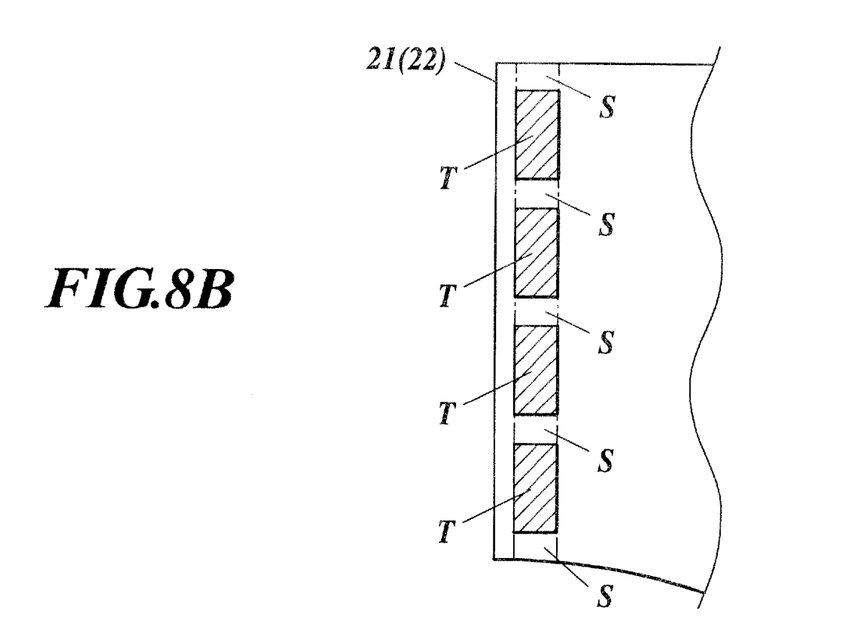
FIG. 8B is a diagram showing a joint section of a paper diaper of modification 2.

As shown in FIG. 8A and FIG. 8B, in the present embodiment, the reduced strength region T and the unreduced strength region S can be provided alternately continuously along the longitudinal direction of the joint sections 21, 22. In other words, the reduced strength region T can be provided intermittently.

Here, each of the area of the reduced strength region T and the unreduced strength region S can be suitably changed. Therefore, the reduced strength region T and the unreduced strength region S can be provided alternately continuously in the same shape (same length) as shown in FIG. 8A or one can be provided to be larger than the other as shown in FIG. 8B.

According to modification 2, partial adjustment of joint strength of the joint sections 21, 22 can be suitably performed.

<Modification 3>

Figure 9A:
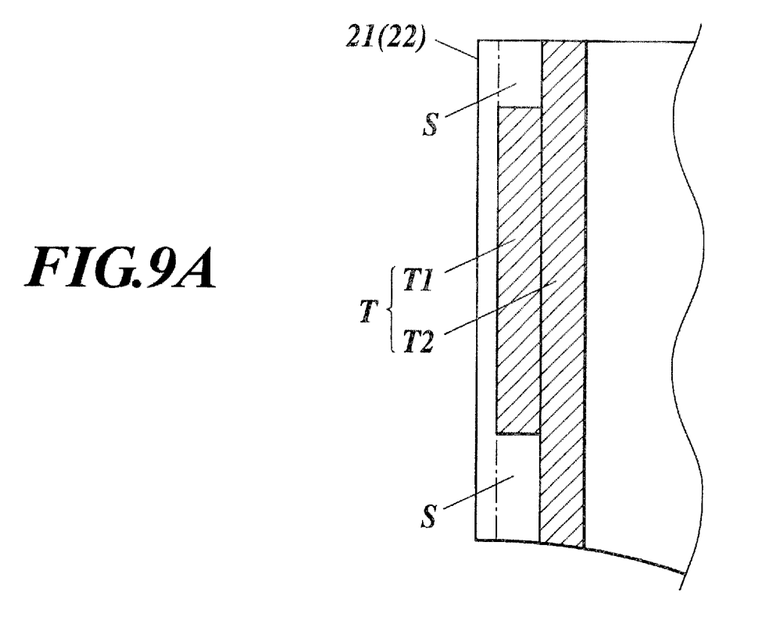
FIG. 9A is a diagram showing a joint section of a paper diaper of modification 3.
Figure 9B:
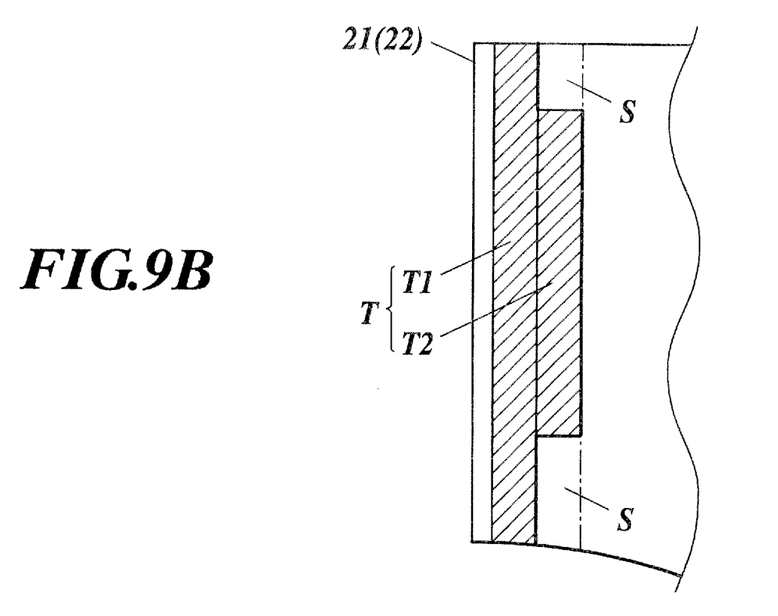
FIG. 9B is a diagram showing a joint section of a paper diaper of modification 3.

As shown in FIG. 9A and FIG. 9B, in the present embodiment, the reduced strength region T can be composed of a first reduced strength section T1 and a second reduced strength section T2 aligned parallel along the width direction of the joint sections 21, 22 and either one of the first reduced strength section T1 or the second reduced strength section T2 can be provided continuously from the upper end portion to the lower end portion of the joint sections 21, 22.

In other words, for example, the unreduced strength region S can be provided in the upper portion and the lower portion of the first reduced strength section T1 and the second reduced strength section T2 can be provided continuously from the upper end portion to the lower end portion of the joint sections 21, 22 as shown in FIG. 9A, or the unreduced strength region S can be provided in the upper portion and the lower portion of the second reduced strength section T2 and the first reduced strength section T1 can be provided continuously from the upper end portion to the lower end portion of the joint sections 21, 22 as shown in FIG. 9B.

Although illustration is omitted, there can be a gap between the first reduced strength section T1 and the second reduced strength section T2.

According to the modification 3, the length of the first reduced strength section T1 and the second reduced strength section T2 can be adjusted to suitably perform partial adjustment of the joint strength of the joint sections 21, 22.

Moreover, since either one of the first reduced strength section T1 or second reduced strength section T2 is provided continuously from the upper end portion to the lower end portion of the joint sections 21, 22, the biological fluid leaking from the side of the paper diaper can be prevented.

<Modification 4>

Figure 10A:
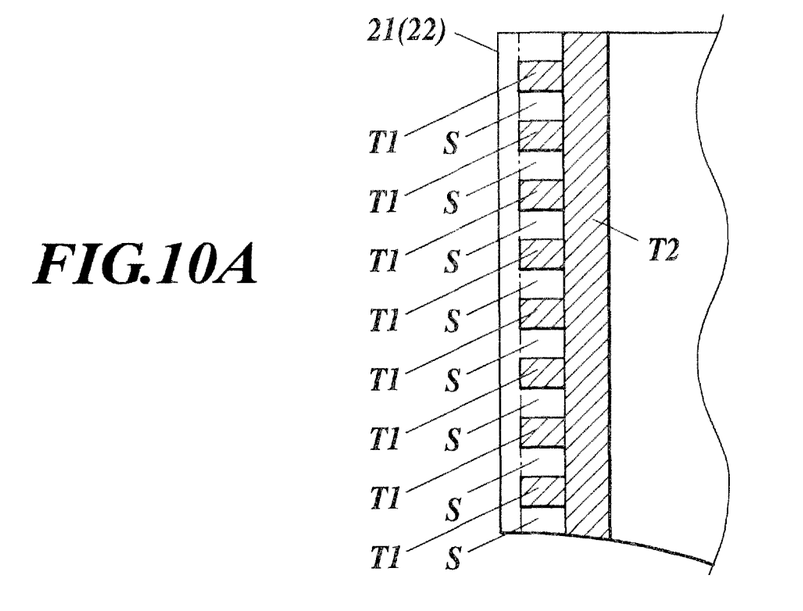
FIG. 10A is a diagram showing a joint section of a paper diaper of modification 4.
Figure 10B:
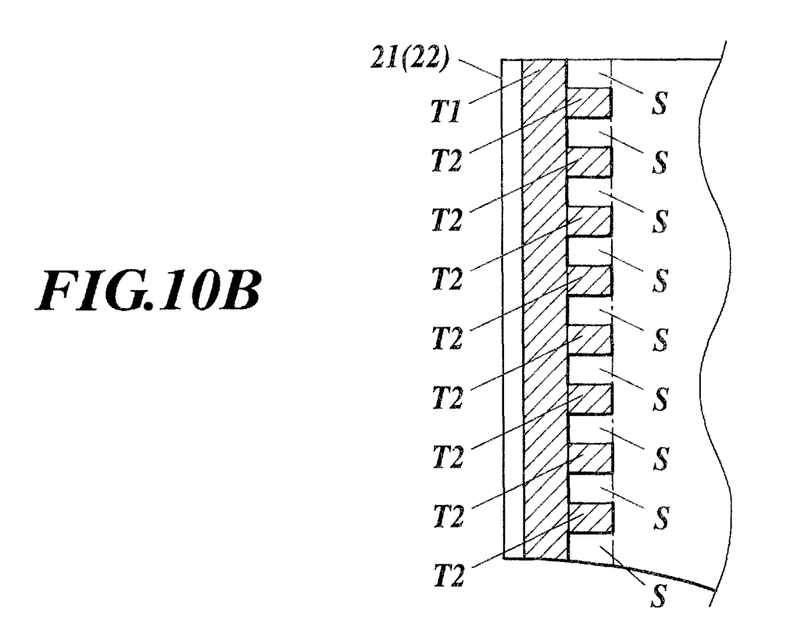
FIG. 10B is a diagram showing a joint section of a paper diaper of modification 4.

As shown in FIG. 10A and FIG. 10B, in the present embodiment, either one of the first reduced strength section T1 or the second reduced strength section T2 can be provided continuously from the upper end portion to the lower end portion of the joint sections 21, 22, and the other can be provided intermittently.

In other words, the second reduced strength section T2 can be provided continuously from the upper end portion to the lower end portion, and the first reduced strength section T1 can be provided intermittently as shown in FIG. 10A, or the first reduced strength section T1 can be provided continuously from the upper end portion to the lower end portion, and the second reduced strength section T2 can be provided intermittently as shown in FIG. 10B.

Although illustration is omitted, there can be a gap between the first reduced strength section T1 and the second reduced strength section T2.

According to the modification 4, the length of the first reduced strength section T1 and the second reduced strength section T2 can be adjusted to suitably perform partial adjustment of the joint strength of the joint sections 21, 22.

Moreover, since either one of the first reduced strength section T1 or second reduced strength section T2 is provided continuously from the upper end portion to the lower end portion of the joint sections 21, 22, the biological fluid leaking from the side of the paper diaper can be prevented.

<Modification 5>

Figure 11A:
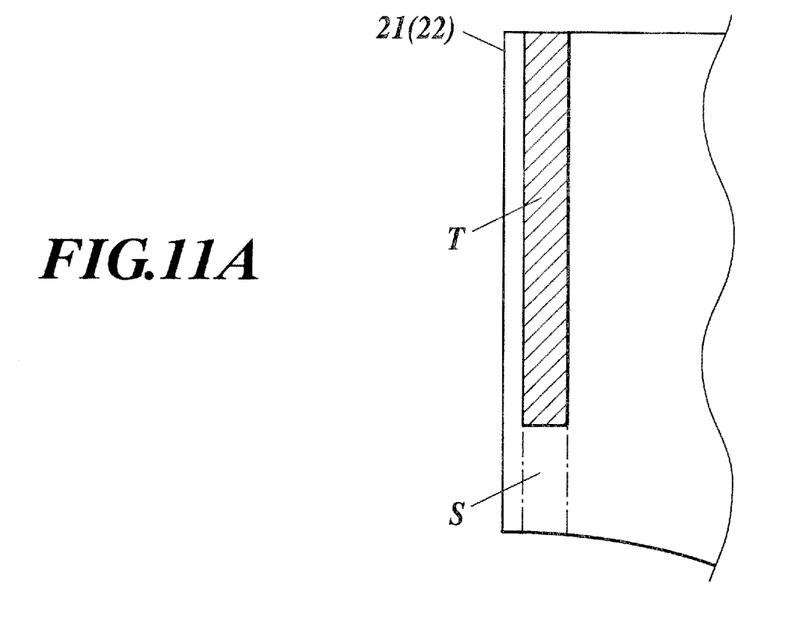
FIG. 11A is a diagram showing a joint section of a paper diaper of modification 5.
Figure 11B:
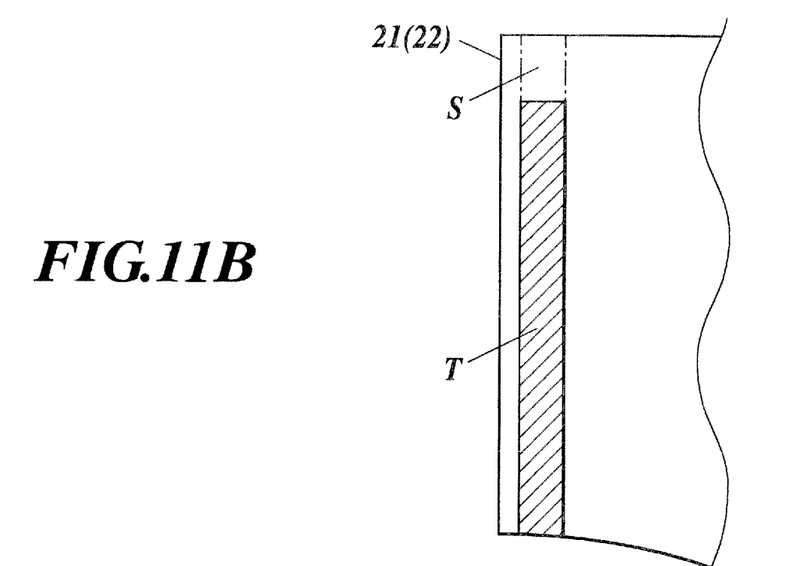
FIG. 11B is a diagram showing a joint section of a paper diaper of modification 5.

As shown in FIG. 11A and FIG. 11B, in the present embodiment, the unreduced strength region S can be provided in either one of the upper end portion or the lower end portion of the joint sections 21, 22.

In other words, the unreduced strength region S can be provided in the lower end portion of the joint sections 21, 22 as shown in FIG. 11A, or the unreduced strength region S can be provided in the upper end portion of the joint sections 21, 22 as shown in FIG. 11B.

Here, the area (length) of each of the reduced strength region T and the unreduced strength region S can be suitably changed.

According to the modification 5, the reduced strength region T can be provided in the upper end portion or the lower end portion of the joint sections 21, 22. Consequently, it is possible to realize a configuration in which it is easy to peel when force is applied to the end portion of the joint sections 21, 22.

Specifically, when the reduced strength region T is provided in the upper end portion as shown in FIG. 11A, there is no adhesive 30 around the leg. Consequently, it is possible to remove roughness around the leg and the fit can be enhanced.

The present invention is not limited to the above embodiment, and can be suitably changed without leaving the scope of the invention.

For example, although illustration is omitted, in the modification 2, the reduced strength region T can be formed in a rhombus shape and the rhombus shaped reduced strength region T can be provided continuously along the longitudinal direction of the joint sections 21, 22. In this case, specifically, the reduced strength region T is provided continuously throughout the entire joint sections 21, 22 so that the tip end portion of the rhombus shape positioned in an up and down direction overlap. Consequently, partial adjustment of joint strength of the joint sections 21, 22 can be suitably performed. Moreover, since the reduced strength region T is provided continuously throughout the entire joint sections 21, 22, the biological fluid leaking from the side of the paper diaper can be prevented.

Although illustration is omitted, in the modification 4, both the first reduced strength section T1 and the second reduced strength section T2 can be provided intermittently from the upper end portion to the lower end portion of the joint sections 21, 22. In this case, the first reduced strength section T1 and the second reduced strength section T2 can be provided alternately.

INDUSTRIAL APPLICABILITY

The present invention can be used in the industry of manufacturing absorptive articles, etc.

DESCRIPTION OF REFERENCE NUMERALS 1 absorptive article (paper diaper)
10 absorptive body
11 liquid permeable surface sheet
12 waterproof sheet
13 absorption body
15 gather nonwoven fabric
16 threadlike elastic stretching member
20 exterior body
20A outer layer sheet
20B torso sheet
20*a* upper layer nonwoven fabric
20*b* lower layer nonwoven fabric
21, 22 joint sections
23 cut line
24 waist elastic member
25 hip elastic member
26 leg elastic member
30 adhesive
F belly-side portion
B back-side portion
M crotch portion
BS standing gather
W hip opening section
L leg opening section
T reduced strength region
S unreduced strength region

The invention claimed is:

1. An absorptive article comprising:
an absorptive body which includes an absorption body; and
an exterior body which is provided to an outer surface side of the absorptive body and which is provided with a belly-side portion which is located on a belly side of a human body when the absorptive article is worn and a back-side portion which is located on a back side of a human body when the absorptive article is worn;

wherein a hip opening section and a pair of left and right leg opening sections are formed in the absorptive article by joining, using heat sealing or ultrasonic sealing, the belly-side portion and the back-side portion of the exterior body at joint sections at both side ends of the belly-side portion and the back-side portion; and wherein the absorptive article includes a reduced strength region, which is disposed with a joint strength reducing material for reducing a joint strength between the joint sections, and an unreduced strength region, which is not disposed with the joint strength reducing material, between the belly-side portion and the back-side portion of the joint sections.

2. The absorptive article according to claim 1, wherein the reduced strength region and the unreduced strength region are provided alternately continuously along a longitudinal direction of the joint section.

3. The absorptive article according to claim 2, wherein:
the reduced strength region includes a first reduced strength section and a second reduced strength section arranged parallel along a width direction of the joint section; and
the first reduced strength section is provided continuously from an upper end portion to a lower end portion of the joint section.

4. The absorptive article according to claim 3, wherein the unreduced strength region is provided at at least one of an upper end portion and a lower end portion of the joint section.

5. The absorptive article according to claim 2, wherein the unreduced strength region is provided at at least one of an upper end portion and a lower end portion of the joint section.

6. The absorptive article according to claim 2, wherein the joint strength reducing material is an adhesive, paper, nonwoven fabric or a base material on which oil agent is applied.

7. The absorptive article according to claim 2, wherein a predetermined color is added to the joint strength reducing material.

8. The absorptive article according to claim 1, wherein:
the reduced strength region includes a first reduced strength section and a second reduced strength section arranged parallel along a width direction of the joint section; and
the first reduced strength section is provided continuously from an upper end portion to a lower end portion of the joint section.

9. The absorptive article according to claim 8, wherein the unreduced strength region is provided at at least one of an upper end portion and a lower end portion of the joint section.

10. The absorptive article according to claim 8, wherein the joint strength reducing material is an adhesive, paper, nonwoven fabric or a base material on which oil agent is applied.

11. The absorptive article according to claim 8, wherein a predetermined color is added to the joint strength reducing material.

12. The absorptive article according to claim 1, wherein the unreduced strength region is provided at at least one of an upper end portion and a lower end portion of the joint section.

13. The absorptive article according to claim 12, wherein the joint strength reducing material is an adhesive, paper, nonwoven fabric or a base material on which oil agent is applied.

14. The absorptive article according to claim 12, wherein a predetermined color is added to the joint strength reducing material.

15. The absorptive article according to claim 1, wherein the joint strength reducing material is an adhesive, paper, nonwoven fabric or a base material on which oil agent is applied.

16. The absorptive article according to claim 15, wherein a predetermined color is added to the joint strength reducing material.

17. The absorptive article according to claim 1, wherein a predetermine color is added to the joint strength reducing material.

* * * * *